(12) United States Patent
Van Wyk

(10) Patent No.: US 6,840,937 B2
(45) Date of Patent: Jan. 11, 2005

(54) ELECTROSURGICAL ABLATOR WITH ASPIRATION

(75) Inventor: Robert A. Van Wyk, Largo, FL (US)

(73) Assignee: Electrosurgery Associates, LLC, Rockville, MD (US)

( * ) Notice: Subject to any disclaimer, the term of this patent is extended or adjusted under 35 U.S.C. 154(b) by 136 days.

(21) Appl. No.: 10/270,572

(22) Filed: Oct. 16, 2002

(65) Prior Publication Data

US 2003/0083655 A1 May 1, 2003

Related U.S. Application Data

(60) Provisional application No. 60/330,006, filed on Oct. 18, 2001, now abandoned.

(51) Int. Cl.[7] .............................................. A61B 18/18
(52) U.S. Cl. .............................. 606/41; 604/35; 606/45
(58) Field of Search .............................. 606/41, 45–50; 604/35, 114; 607/101, 116

(56) References Cited

U.S. PATENT DOCUMENTS

| 5,084,045 A | | 1/1992 | Helenowski | |
| 5,348,555 A | * | 9/1994 | Zinnanti | 606/49 |
| 5,520,685 A | | 5/1996 | Wojciechowicz | |
| 5,681,282 A | * | 10/1997 | Eggers et al. | 604/114 |
| 6,179,836 B1 | | 1/2001 | Eggers et al. | |
| 6,214,003 B1 | | 4/2001 | Morgan et al. | |
| 6,277,112 B1 | * | 8/2001 | Underwood et al. | 606/32 |
| 6,296,638 B1 | * | 10/2001 | Davison et al. | 606/41 |
| 2002/0183741 A1 | * | 12/2002 | Carmel et al. | 606/41 |

FOREIGN PATENT DOCUMENTS

| GB | 1 449 081 A | 9/1976 |
| WO | WO 99/48430 | 9/1999 |
| WO | WO 01/24720 A1 | 4/2001 |

* cited by examiner

Primary Examiner—Michael Peffley
(74) Attorney, Agent, or Firm—Dickstein Shapiro Morin & Oshinsky LLP

(57) ABSTRACT

An aspirating ablator of simple construction and low cost is disclosed. The aspirating ablator is provided with a mandrel connected to a tubular member which houses a suction assembly. An electrode having a rectangular ablation surface formed of multiple parallel ribs or protuberances is assembled onto the mandrel so that the ablation surface is parallel with the longitudinal axis of the mandrel. A ceramic insulator provided with an opening of rectangular shape is assembled to the electrode-mandrel assembly. The insulator is further provided with a cylindrical passage in communication and aligned with a radial passage of the mandrel.

29 Claims, 13 Drawing Sheets

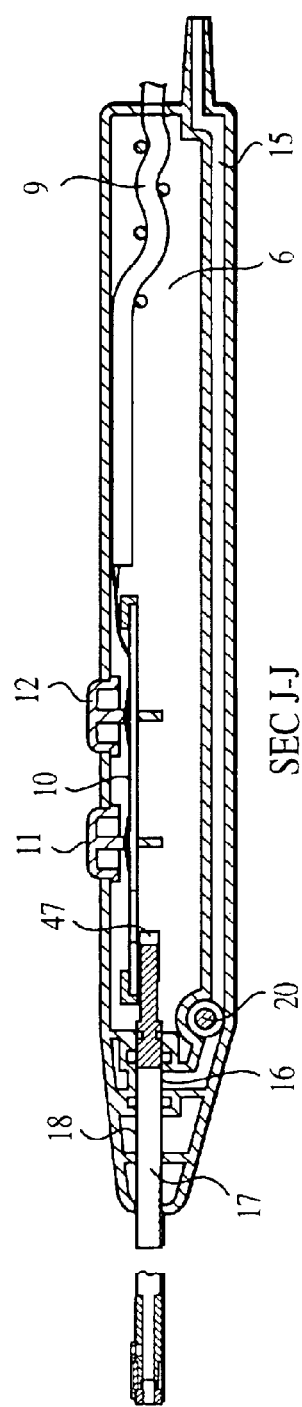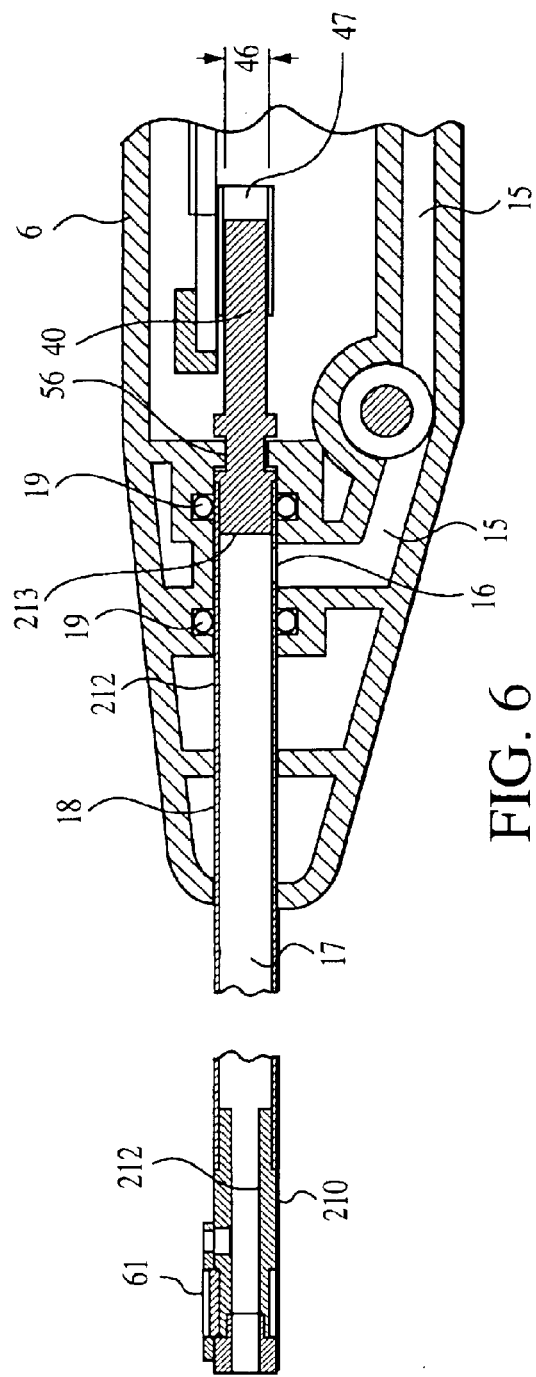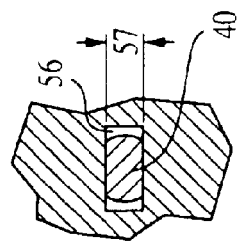

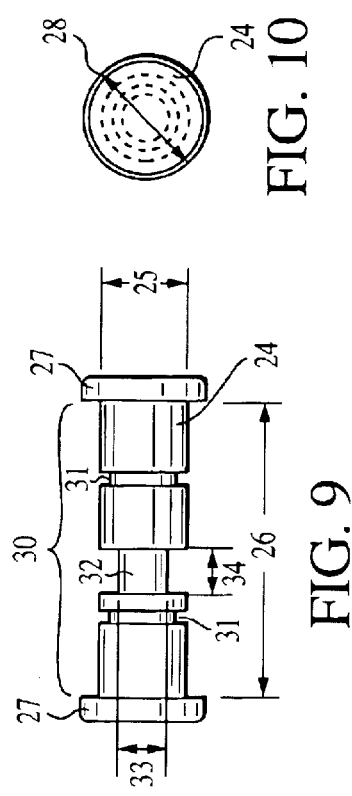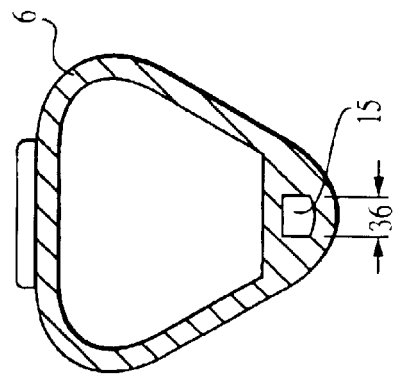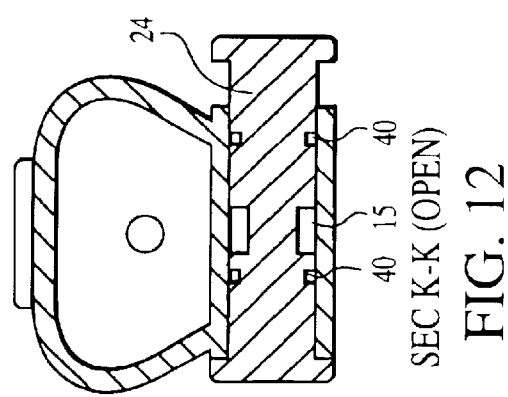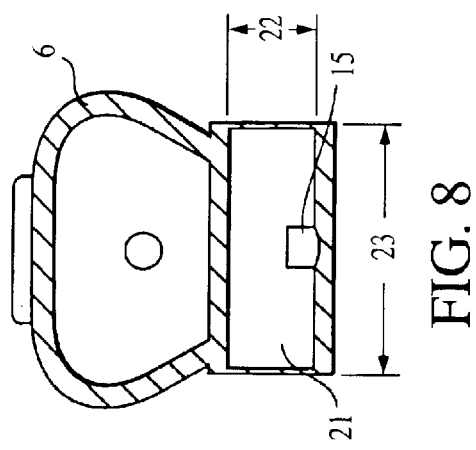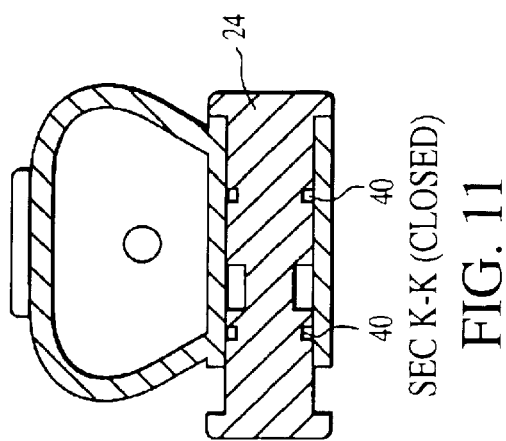

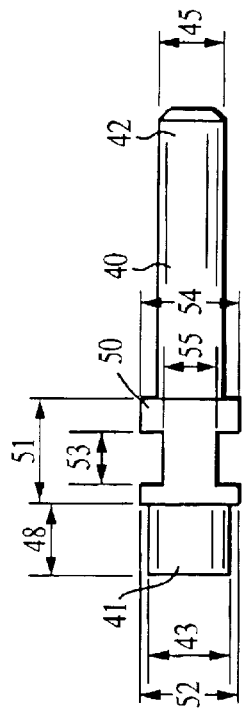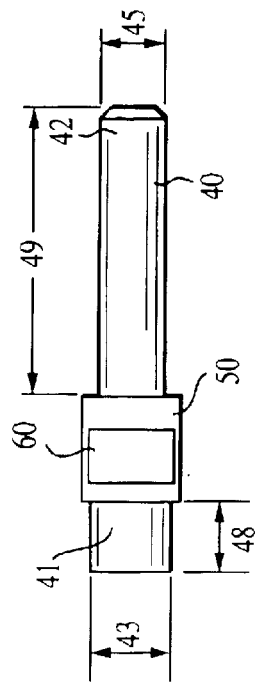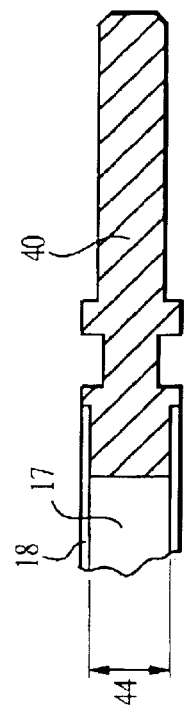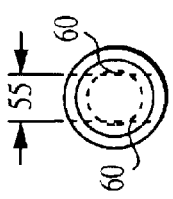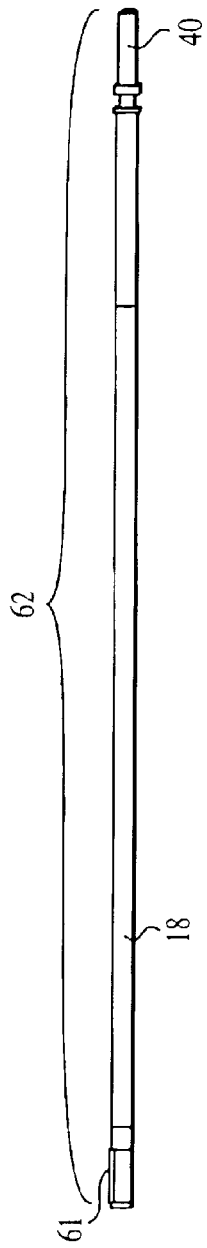
FIG. 14
FIG. 15
FIG. 16
FIG. 17
FIG. 18

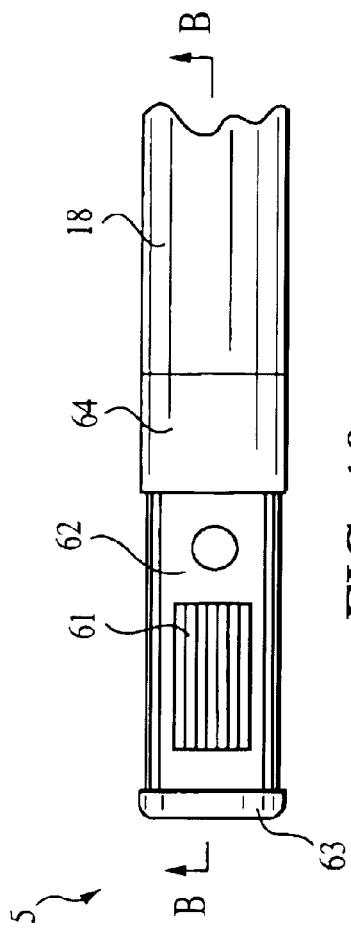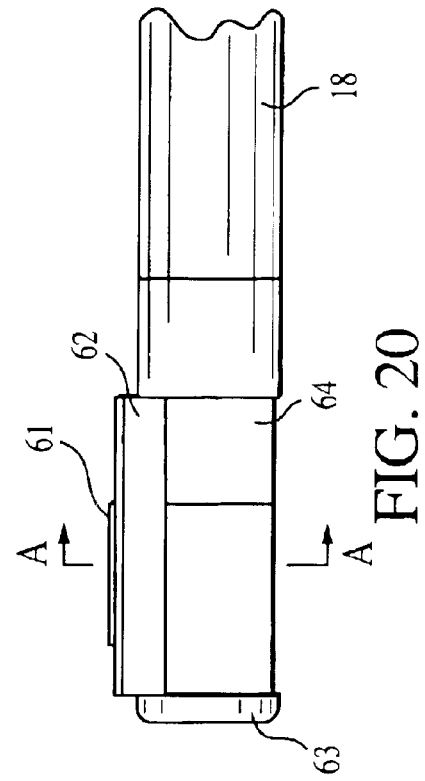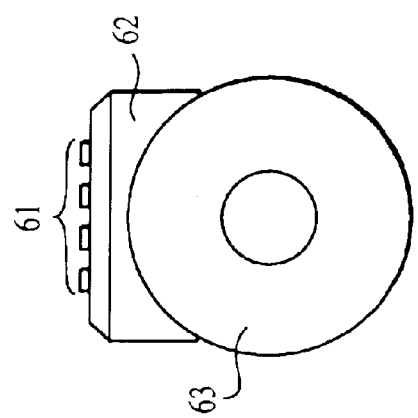

SEC A-A

SEC B-B

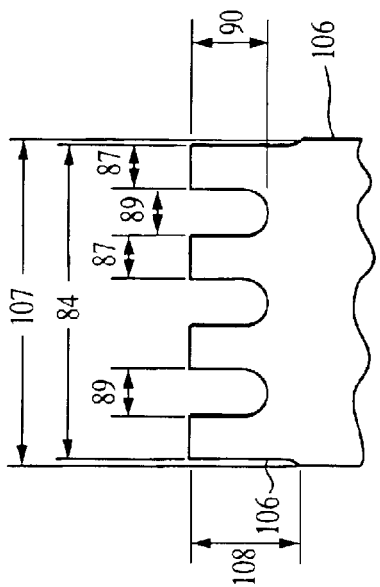
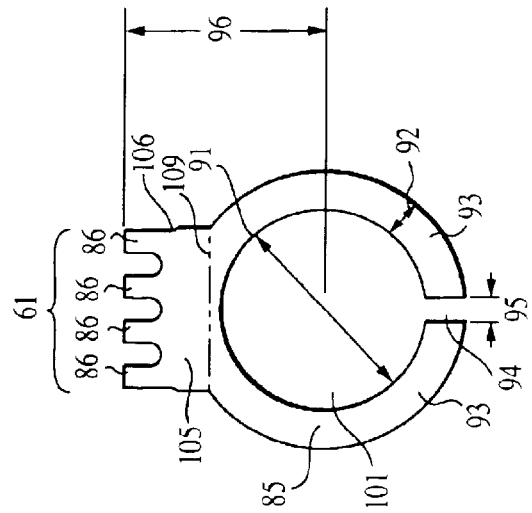
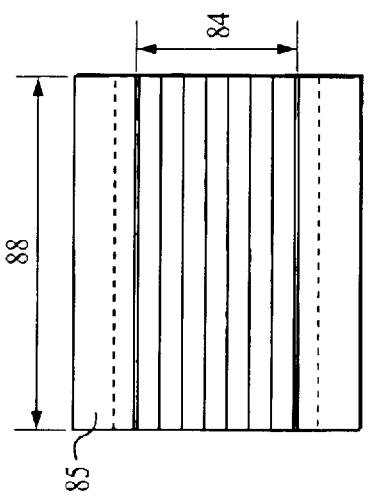

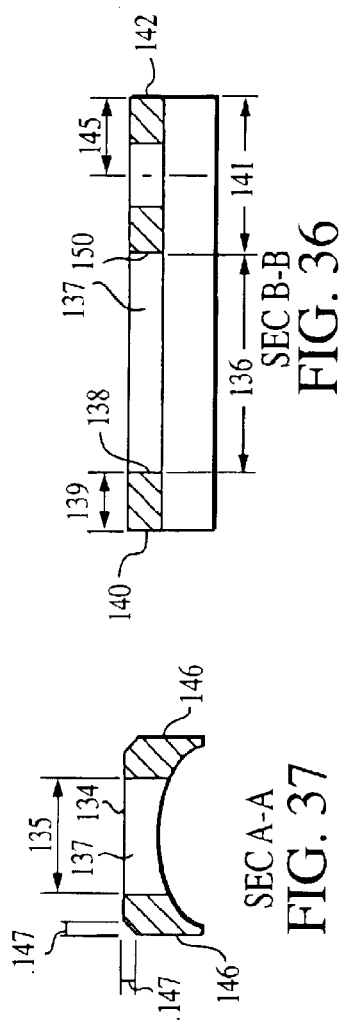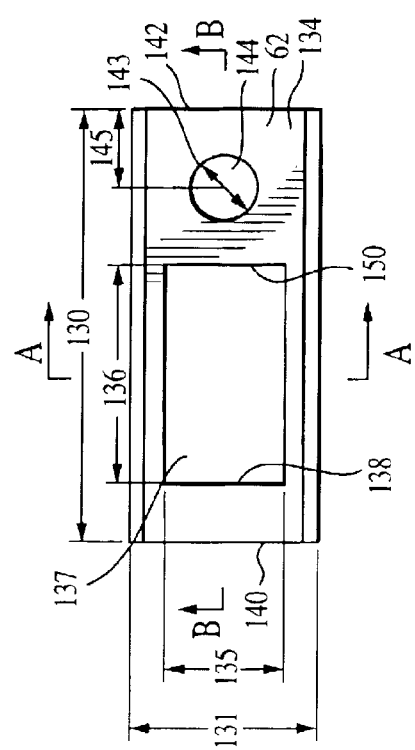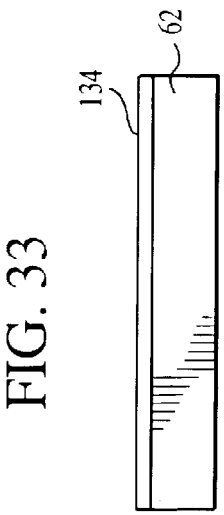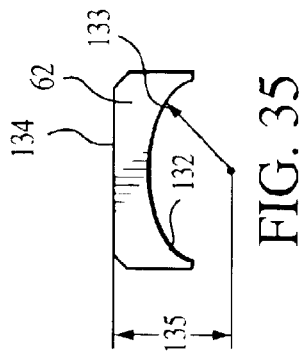

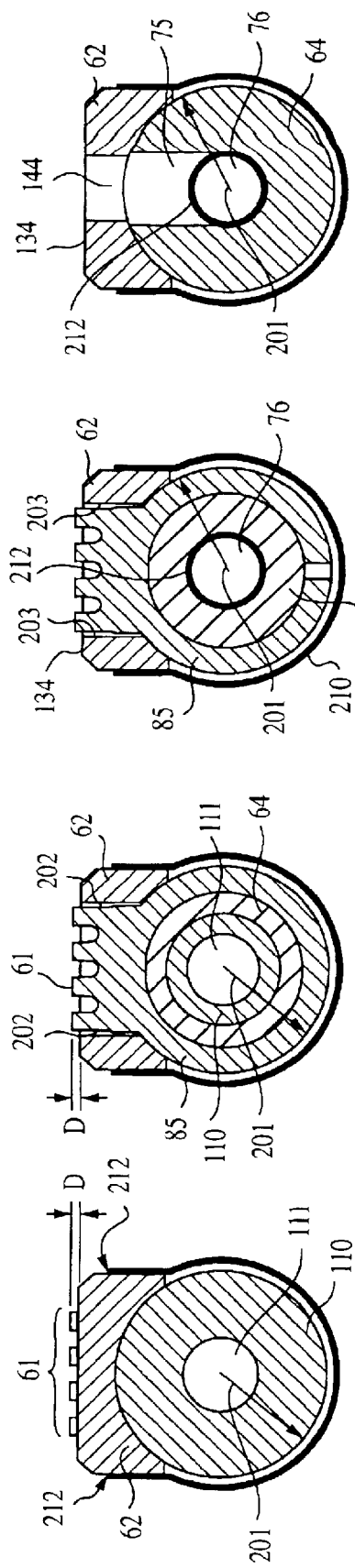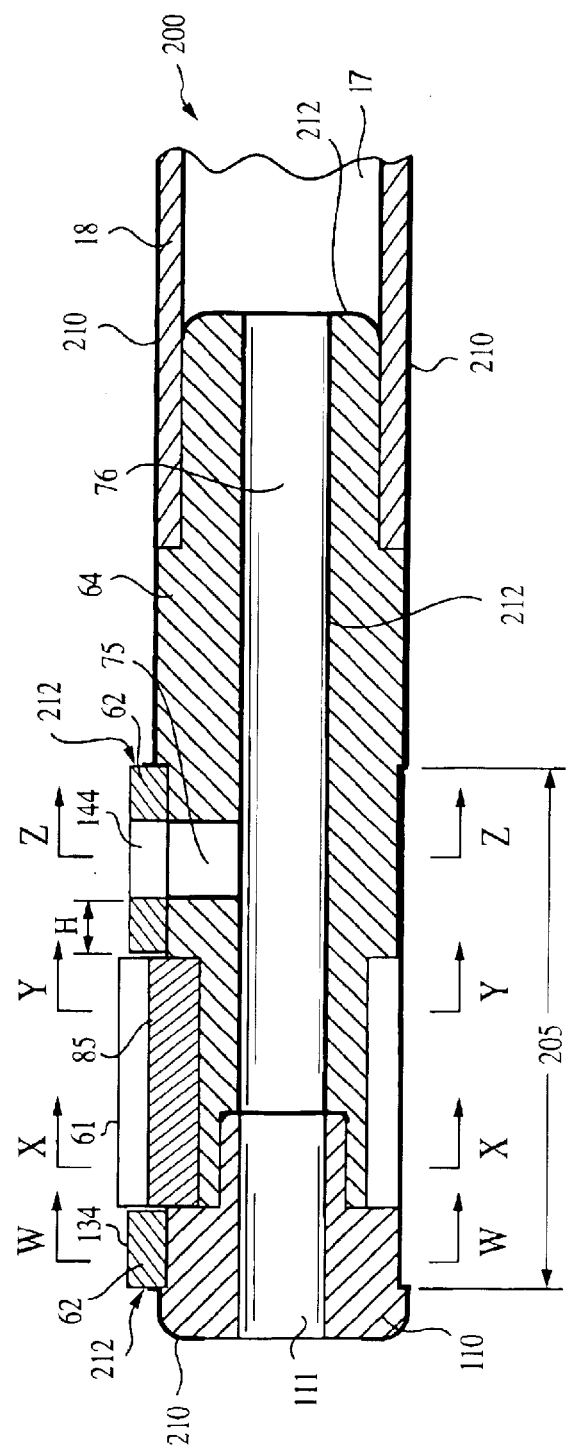

ELECTROSURGICAL ABLATOR WITH ASPIRATION

The present application claims the benefit under 35 U.S.C. 119(e) of U.S. Provisional Application Ser. No. 60/330,006, filed on Oct. 18, 2001, now abandoned, the disclosure of which is incorporated by reference herein.

FIELD OF THE INVENTION

The present invention relates to the field of electrosurgery and, in particular, to electrosurgical devices and methods which employ high frequency voltage to cut, ablate or coagulate tissue in a conductive fluid environment.

BACKGROUND OF THE INVENTION

Least invasive surgical techniques have gained significant popularity because of their ability to accomplish outcomes with reduced patient pain and accelerated return of the patient to normal activities. Arthroscopic surgery, in which the intra-articular space is filled with fluid, allows orthopedic surgeons to efficiently perform procedures using special purpose instruments designed specifically for arthroscopists. Among these special purpose tools are various manual graspers and biters, powered shaver blades and burs, and electrosurgical devices. During the last several years specialized arthroscopic electrosurgical electrodes called ablators have been developed. Exemplary of these instruments are ArthroWands manufactured by Arthrocare (Sunnyvale, Calif.), VAPR electrodes manufactured by Mitek Products Division of Johnson & Johnson (Westwood, Mass.) and electrodes by Oratec Interventions, Inc. (Menlo Park, Calif.). These ablator electrodes differ from conventional arthroscopic electrosurgical electrodes in that they are designed for the bulk removal of tissue by vaporization rather than the cutting of tissue or coagulation of bleeding vessels. While standard electrodes are capable of ablation, their geometries are not efficient for accomplishing this task. While the tissue removal rates of ablator electrodes are lower than those of shaver blades, ablators are used because they achieve hemostasis (stop bleeding) during use and are able to efficiently remove tissue from bony surfaces. Ablator electrodes are used in an environment filled with electrically conductive fluid.

Ablator electrodes are produced in a variety of sizes and configurations to suit a variety of procedures. For example, ablators for use in ankle or elbow arthroscopy are smaller than those used in the knee or shoulder. In each of these sizes, a variety of configurations are produced to facilitate access to various structures within the joint being treated. These configurations differ in the working length of the electrode (the maximum distance that an electrode can be inserted into a joint), in the size and shape of their ablating surfaces, and in the angle between the ablating face and the axis of the electrode shaft. Electrodes are typically designated by the angle between a normal to the ablating surface and the axis of the electrode shaft, and by the size of their ablating surface and any associated insulator.

Primary considerations of surgeons when choosing a particular configuration of ablator for a specific procedure are its convenience of use (i.e., its ease of access to certain structures) and the speed with which the ablator will be able to complete the required tasks. When choosing between two configurations capable of accomplishing a task, surgeons will generally choose the ablator with the larger ablating surface to remove tissue more quickly. This is particularly true for procedures during which large volumes of tissue must be removed. One such procedure is acromioplasty or the reshaping of the acromion. The underside of the acromion is covered with highly vascular tissue which may bleed profusely when removed by a conventional powered cutting instrument such as an arthroscopic shaver blade. Ablator electrodes are used extensively during this procedure since they are able to remove tissue without the bleeding. Ablation in the area under the acromion is most efficiently accomplished using an electrode on which a line normal to the ablating surface is perpendicular to the axis of the ablator shaft. Such an electrode is designated as a "90 Degree Ablator" or a "side effect" ablator. Exemplary of such electrodes are the "3.2 mm 90 Degree Three-Rib UltrAblator" by Linvatec Corporation (Largo, Fla.), the "90 Degree Ablator" and "90 Degree High Profile Ablator" by Oratec Interventions, the "Side Effect VAPR Electrode" by Mitek Products Division of Johnson and Johnson, and the "3.5 mm 90 Degree Arthrowand," "3.6 mm 90 Degree Lo Pro Arthrowand," and "4.5 mm 90 Degree Eliminator Arthrowand" by Arthrocare Corporation.

The above-mentioned 90 degree ablator electrodes may be divided into two categories: (i) electrodes of simple construction, wherein RF energy is conducted to the ablator tip by an insulated metallic rod or tube; and (ii) electrodes of complex construction, which use wires to conduct power to the tip.

Ablator electrodes having a simple geometry are produced by Linvatec Corporation (as described in U.S. Pat. No. 6,149,646) and Oratec Interventions, Inc. and are monopolar instruments, that is, the circuit to the electrosurgical generator is completed by a dispersive pad (also called a return pad) placed on the patient at a distance from the surgical site. A suitable geometry, either ribbed or annular, is formed on the distal end of the ablator rod, and the distal tip of the rod is bent to a predetermined angle to the axis of the rod. For a 90 degree electrode, this predetermined angle is 90 degrees. The rod diameter may be locally reduced in the region near its distal tip to reduce the radius of the bend. The rod is insulated up to the ablation face on the rod distal tip using polymeric insulation. A ceramic insulator may be added to prevent charring of the polymeric insulation.

Ninety degree ablator electrodes having a complex construction, such as those in which the active electrode is attached to the electrosurgical generator via cables passing through an elongated tubular member, are produced by Arthrocare Corporation (U.S. Pat. No. 5,944,646 and others) and the Mitek Products Division of Johnson & Johnson. Typically, these electrodes are bipolar instruments, having a return electrode on the instrument in close proximity to the active electrode. Bipolar arthroscopy electrodes of this type are constructed of a tubular member upon which one or more electrodes (herein referred to as active electrodes) are mounted and connected via one or more cables to an electrosurgical generator, the leads passing through the lumen of the tubular member. The active electrodes are isolated electrically from the tubular member and rigidly mounted to the tubular member by a ceramic insulator affixed to the tubular member. The tubular member is electrically isolated from the conductive fluid medium by a polymeric coating, except for an area at the distal tip in the vicinity of the active electrode. The proximal end of the tubular member is connected electrically to the electrosurgical generator via one or more cables. During use, current flows from the active electrode through the conductive fluid medium to the uninsulated portion of the tubular member, which functions as a return electrode in close proximity to the active electrode.

While the construction of these complex bipolar electrodes is more expensive than that of the other monopolar electrodes, this construction allows the design of 90 degree ablators with large ablating surfaces, the surfaces being only slightly elevated above the outer surface of the tubular member. This "low profile" design is desirable in that it allows surgeons to pass the electrode through smaller diameter cannulae than would be possible with electrodes of other designs.

Electrodes of simple design and having a single-piece rod with far distal bend for an active electrode have certain design limitations with regard to the positioning of the ablating surfaces. Low profile, 90 degree designs require that the bend radius be extremely tight and placed in extremely close proximity to the ablating surfaces. Such a bend may be accomplished by reducing the cross-sectional area of the rod in the area to be bent. Alternatively, extra length may be added to the distal tip of the rod, the rod bent and the extra material removed prior to forming of the ablation surfaces.

Each of these approaches has limitations. First, in the case of reduced cross-sectional area, the active electrode of an ablator device becomes very hot during use because of interaction of the ablative arc with the metal of the electrode. During use, a portion of the electrode is lost due to vaporization of the material. Melting of the polymeric insulation on the ablator rod may occur if the temperature of the metal rod becomes excessively high. This melting may be minimized in the region adjacent to the ablating surface through use of a ceramic insulator between the active electrode and the polymeric insulation. Cooling of this region also occurs through conduction of heat away from the region proximally through the electrode rod. The degree of cooling depends on the cross-sectional area of the electrode rod. By reducing the cross-sectional area of the rod to achieve a far distal bend, the temperature of the electrode in the region adjacent to the ablating surface is increased and melting of the polymeric insulation may occur.

Second, when extra material is added to the rod to permit bending and then machined away so as to allow forming of the ablating surfaces, any but the simplest active electrode geometry will require complex machining operations. For instance, to produce a ribbed geometry with a ceramic insulator, such as that of the Linvatec 3-Rib ablator, the extra material must first be removed, a precise cylindrical surface perpendicular to the axis of the rod formed to allow installation of the ceramic insulator and, finally, the ribs formed by grinding or wire EDM. Each of these operations requires that the rod be precisely and repeatably located, a difficult task on an item such as a bent rod.

As mentioned previously, interaction of the ablative arcs with the active electrode causes material loss through vaporization and combustion of the metallic material. Combustion of the electrode material will affect the characteristics of the plasma of which the arc is composed. In some cases, it is desirable to use a combustible electrode material such as titanium to achieve certain desired ablation process characteristics. For instance, it is thought that the extreme brightness of the arc causes some photoablation of tissue. This photoablation may be maximized by increasing the brightness of the arc. In turn, this increase in brightness may be achieved by using a combustable electrode material such as titanium. Ablators of complex construction are able to easily use a variety of active electrode materials because the electrodes are a small part of a larger complex assembly. On electrodes of simple construction, the selection of the active electrode material is not as simple since the entire electrode rod is made from the same material as the active electrode tip. Use of a material like titanium can add significantly to the material cost and the machining cost of the product.

A recent addition to ablator electrodes is a means of aspiration to remove bubbles from the surgical site. During arthroscopic electrosurgery, tissue is vaporized producing steam bubbles which may obscure the view of the surgeon or displace saline from the area of the intra-articular space which the surgeon wishes to affect. During ablation, the amount of bubbles produced is even greater than the amount produced when using other electrodes, since fluid is continually boiling at the active electrode during use. Ideally, flow through the joint carries these bubbles away. Nevertheless, in certain procedures, this flow is frequently insufficient to remove all of the bubbles. The aspiration means on an aspirating ablator removes some bubbles as they are formed by the ablation process, and others after they have collected in pockets within the joint. The ablator aspiration means is connected to an external vacuum source which provides suction for bubble evacuation.

There are two types of aspiration on currently available ablator products, which may be divided into two categories according to their level of flow.

High-flow ablators have an aspiration tube having an diameter larger than the elongated distal portion of the probe and coaxial with the axis of the ablator elongated portion so as to form a passage between the elongated portion and the aspiration tube. Bubbles and fluid are drawn into the passage through the distal opening and/or openings formed in the tube wall near its distal tip. High-flow ablators may decrease the average joint fluid temperature by removing heated saline (waste heat since it is an undesirable byproduct of the process) from the general area in which ablation occurs. The effectiveness of the aspiration, both for removal of bubbles and for removal of waste heat, will be affected by the distance between the opening through which aspiration is accomplished and the active electrode. The distal tip of the aspiration tube is generally several millimeters distant proximally from the active electrode, so as to not to obstruct the surgeon's view of the electrode during use. Decreasing this distance is desirable since doing so will increase the effectiveness of the aspiration, however, this must be accomplished without limiting the surgeon's view or decreasing the ablators ability to access certain structures during use.

Low-flow ablators aspirate bubbles and fluid through gaps in the ablating surfaces of the active electrode and convey them from the surgical site via a tube passing through the ablator tubular member, or via a cannulation in the ablator rod. A low-flow ablator will require increased power to operate as effectively as a high-flow aspirating ablator because the low-flow aspiration is drawing hot saline from the active site of a thermal process. In the case of low-flow ablators, the heat removed is necessary process heat rather than the waste heat removed by high-flow ablators. As a result, low-flow aspirating ablators generally require higher power levels to operate than other ablators, thereby generating more waste heat and increasing undesirable heating of the fluid within the joint.

Each of the above-described aspirating ablators has its drawbacks. In high-flow aspirating ablators, the aspiration tube increases the diameter of the device and requires the use of larger cannulae. In low-flow aspirating ablators, the devices frequently clog with charred tissue.

Accordingly, it is an object of this invention to produce a low-cost monopolar electrosurgical ablator electrode of simple construction, having RF energy conducted to the active electrode through the material of the elongated member, and having a large ablating surface and a low profile with the ablation surface displaced only a small distance above the periphery of the outer surface of the elongated body.

It is also an object of this invention to produce a monopolar electrosurgical ablator of simple construction and comprising an active electrode which may be of a material different from the material forming the elongated body of the electrode.

It is also an object of this invention to produce a monopolar electrosurgical ablator electrode having a high-flow aspiration means, which does not increase the diameter of the electrode elongated portion and which is provided with multiple openings in the ablator distal tip area, at least one of which is in close proximity to the active electrode.

SUMMARY OF THE INVENTION

The present invention provides an aspirating ablator of simple construction having a proximal portion forming a handle and an elongated tubular distal portion, the distal tip of which is formed to an ablating surface.

The elongated tubular member of the aspirating ablator electrode of the present invention comprises a stainless steel tube provided at its proximal end with an alignment/connector piece, which provides angular alignment of the tube relative to the handle. At its distal end, the tube is provided with a mandrel connected to the tube. The mandrel has a tubular shape, having an inner lumen and a cylindrical external shape. A cylindrical passage extends from the inner lumen radially upward to the upper surface of the mandrel a short distance distal from the end of the stainless tube. An electrode piece of stainless steel, titanium or other metallic material has a tubular section with an inner diameter suitable for assembly onto the mandrel and a rectangular ablation surface formed of multiple parallel ribs or protuberances separated by grooves. The electrode piece is assembled onto the mandrel so that the ablation surface is parallel with the upper surface of the handle, and the intersection of the radial passage with the mandrel upper surface is positioned proximally for less than about 1 centimeter from the proximal end of said ablation surface. A ceramic or polymeric tip cap is attached at the end of the mandrel, the tip cap having a cylindrical passage which is coaxial with the lumen in the mandrel, thereby providing a means for suction supplied to the tubular member to aspirate materials in the proximity to the distal-most face of the tip cap. The inner lumen of the tubular member and mandrel and mandrel radial passage are covered with an insulating material so as to prevent contact between fluid and metallic surfaces.

A ceramic insulator is assembled to the electrode-mandrel assembly. When viewed in plan view, the ceramic insulator has a rectangular shape and two openings therein, the first opening being rectangular and slightly larger in length and width than the ablation surface, the second being round and positioned proximal to the rectangular opening by a distance equal to that between the electrode assembled onto the mandrel and the radial passage in the mandrel. When viewed axially, the lower surface of the insulator has a radial shape, the radius of which is equal to half the outer diameter of the electrode tubular portion. The insulator is positioned on the electrode-mandrel assembly so that the ablator surface protrudes through the rectangular opening in the insulator with the ribs or protuberances extending about 0.1 to about 2 millimeters above the top surface of the insulator. The cylindrical passage in the insulator is aligned with the radial passage in the mandrel to allow aspiration from the region proximal to the electrode through the passage created by the cylindrical passage in the insulator, the radial passage in the mandrel, the inner lumen of the tube and the passage in the handle to the external vacuum source.

In another embodiment, the electrode is integral with the mandrel. In this embodiment the entire electrode/mandrel component is preferably made from the desired electrode material. The component may be made either by turning on a Swiss-style screw machine followed by secondary machining of grooves in the electrode surface, or by metal injection molding. Although the latter process requires machining of an injection mold, it is able to produce precise, complex, metal shapes from metallic materials at very low costs.

In another embodiment, the electrode is integral with the mandrel as in the previous embodiment, however, the ribs or protuberances of the active electrode are circumferential rather than axial, and lateral-facing surfaces of the electrode are angled to be tangential to the component's cylindrical section. This configuration allows the assembled component to be made complete on a Swiss-style screw machine with no secondary operations required, thereby lowering the manufacturing cost. Alternatively, metal injection molding may be used to produce the component. An advantage of this embodiment is that, during production scale-up, the component may be manufactured at low cost by machining until sales volumes are sufficient to justify the cost of an injection mold to achieve further cost savings.

BRIEF DESCRIPTION OF THE DRAWINGS

FIG. 5 is a lateral sectional view of the structure of FIG. 1.

FIG. 6 is an expanded sectional view of the distal region of FIG. 1.

FIG. 7 is an axial sectional view of alignment features of the tubular section assembly and handle assembly of FIG. 1.

FIG. 8 is an axial sectional view of the handle body portion of the suction control.

FIG. 9 is a lateral view of the movable portion of the suction control.

FIG. 10 is an axial view of the structure of FIG. 9.

FIG. 11 is an axial sectional view of the suction control in the closed position showing fixed and movable portions.

FIG. 12 is an axial sectional view of the suction control in the open position showing fixed and movable portions.

FIG. 13 is an axial sectional view of the handle showing the aspiration passage.

FIG. 14 is a plan view of the tube assembly proximal alignment connector.

FIG. 15 is a side view of the structure of FIG. 14.

FIG. 16 is an axial view of the structure of FIG. 14.

FIG. 17 is a sectional view of the structure of FIG. 14.

FIG. 18 is a side view of the tubular assembly with ablator tip and proximal alignment connector.

FIG. 19 is a plan view of the ablator tip assembly.

FIG. 20 is a side view of the structure of FIG. 19.

FIG. 21 is an axial view of the structure of FIG. 19.

FIG. 27 is a plan view of the electrode.

FIG. 28 is a side view of the structure of FIG. 27.

FIG. 29 is an axial view of the structure of FIG. 27.

FIG. 30 is an expanded view of the upper portion of the structure of FIG. 29.

FIG. 33 is a plan view of the insulator.

FIG. 34 is a side view of the structure of FIG. 33.

FIG. 35 is an end view of the structure of FIG. 33.

FIG. 36 is a side sectional view of the structure of FIG. 33.

FIG. 37 is an axial sectional view of the structure of FIG. 33.

FIG. 41 is a side sectional view of the structure of FIG. 39.

FIG. 42 is an axial sectional view of the structure of FIG. 41 taken along line Z—Z.

FIG. 43 is an axial sectional view of the structure of FIG. 41 taken along line Y—Y.

FIG. 44 is an axial sectional view of the structure of FIG. 41 taken along line X—X.

FIG. 45 is an axial sectional view of the structure of FIG. 41 taken along line W—W.

DETAILED DESCRIPTION OF THE PREFERRED EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized, and that structural, logical and electrical changes may be made without departing from the spirit and scope of the present invention.

Figure 1:
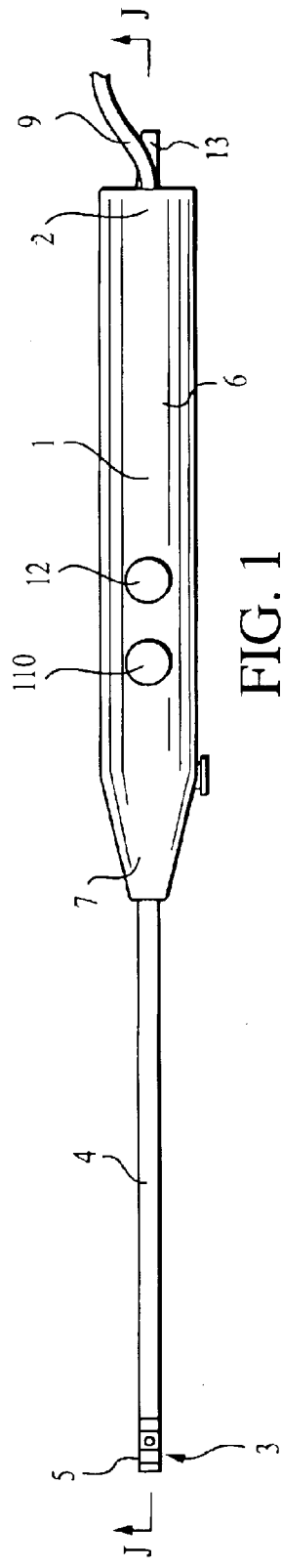
FIG. 1 is a plan view of an aspirating ablator constructed in accordance with the present invention.
Figure 2:
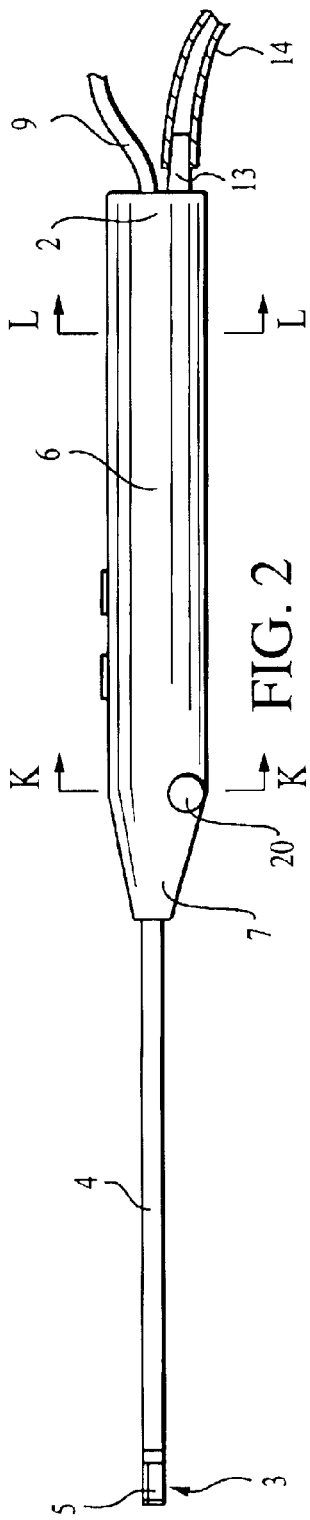
FIG. 2 is a side view of the structure of FIG. 1.
Figure 3:
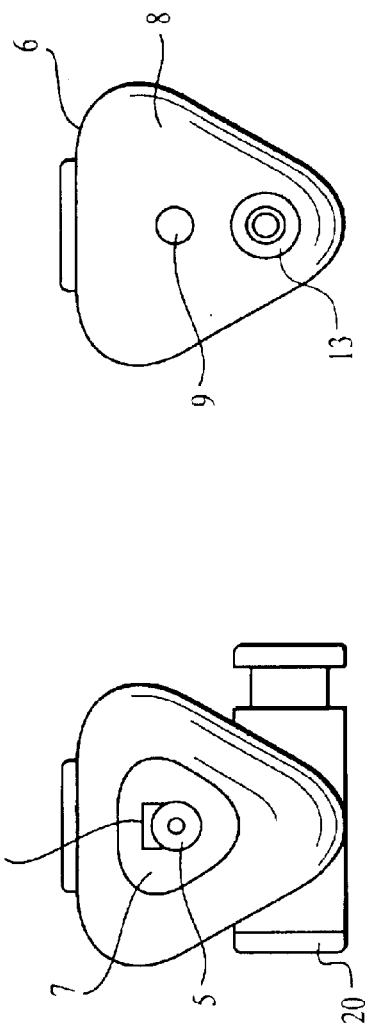
FIG. 3 is an expanded distal end view of the structure of FIG. 1.
Figure 4:
FIG. 4 is an expanded proximal end view of the structure of FIG. 1.

Referring now to the drawings, where like elements are designated by like reference numerals, FIGS. 1 and 2 illustrate an aspirating ablator 1 constructed in accordance with the present invention and having a proximal end 2, a distal end 3, an elongated distal portion 4 terminating in an electrode assembly 5 suitable for arthroscopic ablation of tissue, and a proximal portion 6 that forms a handle. The handle 6 has a proximal end 2 and a distal end 7 (also shown in FIG. 3). An elongated distal portion 4 protrudes from the distal end 7 of the handle 6. The proximal end 2 of the handle 6 has a proximal face 8 (also shown in FIG. 4) from which passes an electrical cable 9 for connection to an electrosurgical generator (not shown). As illustrated in FIG. 5, the electrical cable 9 is connected to a switch 10 so that an electrosurgical generator may be activated by depressing "ABLATE" button 11 or "COAG" button 12, both protruding from the upper surface of handle 6. Thus, depressing the "ABLATE" button activates said electrosurgical generator thereby supplying Radio Frequency (RF) energy of the desired waveform to the elongated portion of the instrument. In the same manner, depressing the "COAG" button supplies RF energy of the appropriate waveform to the elongated portion of the instrument.

Referring back to FIGS. 1, 2, and 4, a tapered tubular section 13 passes from proximal surface 8. A tube 14 may be connected to the tapered tubular section 13, the opposite end of the tube being attached to an external vacuum source to provide suction to the handpiece. As illustrated in FIGS. 5 and 6, vacuum supplied to the handpiece is transmitted via passage 15 and opening 16 to inner lumen 17 of tubular section 18. The passage 15 is molded into the interior of the handle 6. Leakage of the vacuum between tube 18 and handle 6 is prevented by o-rings 19. The level of suction applied to inner lumen 17 of tubular section 18 is controlled by flow control valve 20 having a cylindrical section 21 of diameter 22 and length 23 in handle 6 (FIG. 8), the inner lumen of the cylindrical section 21 intersecting passage 15, and a slide 24 (FIGS. 9 and 10) having a cylindrical section 30 of diameter 25 and length 26. The diameter 25 is slightly smaller than diameter 22, and the length 26 is greater than length 22. Diameter 25 is terminated at each end by a short section 27 of diameter 28, diameter 28 being greater than diameter 22. The axis of the flow control valve 20 is perpendicular to the longitudinal axis of the handle 6.

Positioned within the cylindrical section of slide 24 are two grooves 31 appropriately sized for o-rings 40 and a cylindrical section 32 of diameter 33 and length 34, the diameter 33 being smaller than the diameter 25 and the length 34 being greater than the width 36 of passage 15. Cylindrical section 32 is positioned axially within cylindrical section 30. In this manner, when the slide 24 is assembled within the cylindrical section 21 of the handle 6 (FIGS. 11 and 12), positioning the slide 24 at the extremity of its travel will result in blockage of passage 15 (shown in FIG. 11). In contrast, positioning the slide 24 at the other extreme of its travel allows flow through channel 15 (shown in FIG. 12).

As seen in FIG. 18, the proximal end of tubular section 18 is provided with an alignment connector 40. The alignment connector 40 (FIGS. 14–16) has a distal portion 41 and a proximal portion 42, the distal portion having length 48 and being cylindrical of a diameter 43 slightly greater than diameter 44 of the tubular section 18 (FIG. 17). Proximal portion 42 of length 49 is cylindrical in shape having a diameter 45 slightly greater than diameter 46 of connector 47 of switch 10 (FIG. 6). Referring back to FIGS. 14–16, portion 50 of length 51 and diameter 52 is formed between distal portion 41 and proximal portion 42. Two slots of width 53 and depth 54 are formed within portion 50 to form a segment with parallel planar faces 60 and thickness 55, the thickness 55 being smaller than width 57 of slot 56 of handle 6 (FIG. 7).

Referring to FIG. 18, the alignment connector 40 is assembled to tubular section 18 by pressing distal portion 41 into inner lumen 17 so that planar faces 60 becomes parallel to ablation surface 61. As illustrated in FIG. 6, alignment of ablation surface 61 with the top surface of handle 6 is ensured by engaging parallel surfaces 60 with slot 56 of handle 6. Proximal portion 42 of alignment connector 40 engages connector 47 of switch 10 to provide electrical connection between the switch 10 and the tubular section 18.

Referring now to FIGS. 19–21, the electrode assembly 5 comprises a ribbed ablation surface 61, an insulator 62, an end cap 63, and a mandrel 64. Referring to FIGS. 22–26, the mandrel 64 is tubular with one inner lumen 76 of diameter 77 and comprises four segments, each having a unique diameter. A first, proximal-most segment 65 of length 66 has a diameter 67 slightly larger than the inner diameter 44 of the tubular section 18 (FIG. 17). A second, distal-most segment 68 of length 69 has a diameter 70. A third segment 71, immediately proximal to segment 68 has a length 72, a radius 73, and a radial passage 75 having a diameter 74 and located at a distance 79 from distal tip 78, the radial passage intersecting inner lumen 76. The radial step 100 between segments 68 and 71 is equal to half the difference in diameters of the two segments. A fourth segment 80, immediately distal to the proximal-most segment 65, has a length 81 and a diameter 82. Distal-most segment 102 of inner lumen 76 has a diameter 103 and length 104. Mandrel 64 may be formed, for example, of stainless steel material 83.

Referring to FIGS. 27–30, the ablating surface 61 of width 84 and length 88 is the top surface of electrode 85, the ablating surface 61 being provided with a series of ribs or protuberances 86 of width 87 and separated by grooves of width 89 and depth 90. Although the ribs or protuberances 86 of FIG. 29 are illustrated as having a rectangular shape, the invention contemplates ribs or protuberances of various cross-sectional geometries or configuration, for example, square, trapezoidal, triangular, or hexagonal, among many others. Width 89 is of about 0.1 to about 2 millimeters, more preferably of about 0.2 to about 0.4 millimeters.

Figure 22:
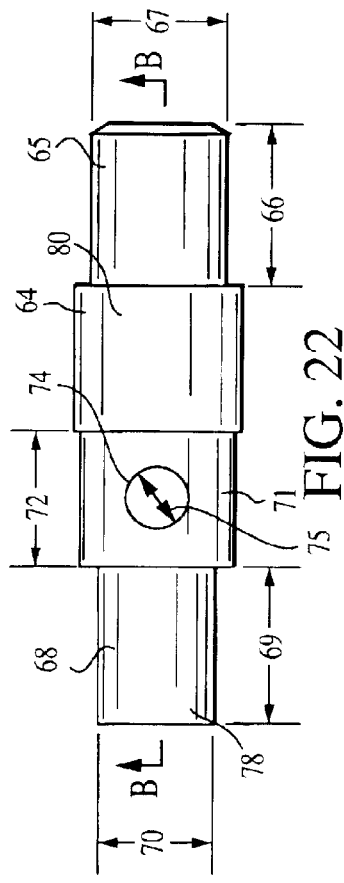
FIG. 22 is a plan view of the tip mandrel.
Figure 24:
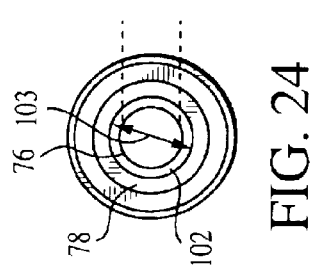
FIG. 24 is an axial view of the structure of FIG. 22.
Figure 23:
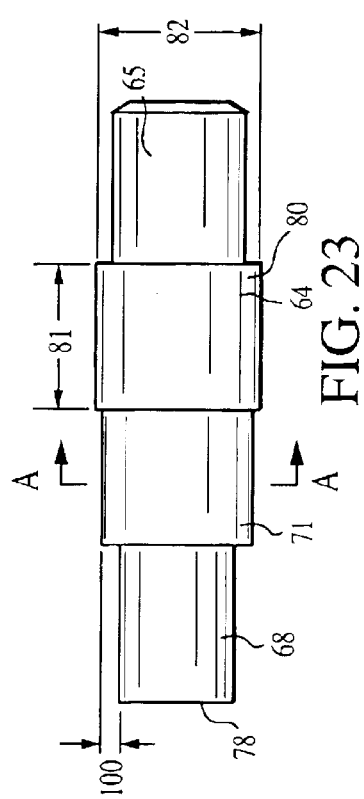
FIG. 23 is a side view of the structure of FIG. 22.
Figure 26:
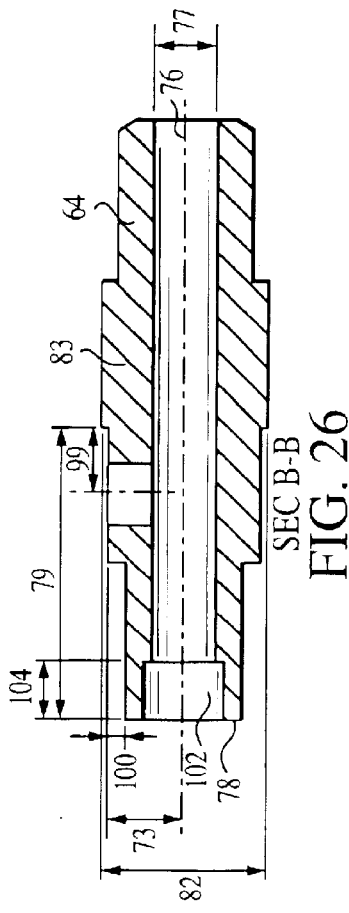
FIG. 26 is a lateral sectional view of the structure of FIG. 22.

As illustrated in FIG. 29, the electrode 85 has two distinct regions, a rectangular region 105 bounded by the ablating surface 61, lateral facing surfaces 106, and a line 109 drawn between the lower ends of lateral facing surfaces 106, and a cylindrical region 93 of thickness 92 defining inner lumen 101 of diameter 91, the diameter 91 being smaller than the diameter 70 of the distal-most segment 68 of the mandrel 64 (FIGS. 22 and 26). As shown in FIG. 29, the thickness of the electrode 85 is ablating surface length 88 which is equal to the length 69 of the distal-most segment 68 of the mandrel 64 (FIG. 22). Thickness 92 is equal to the radial step 100 between the segments 68 and 71 of the mandrel 64 (FIG. 23). A slot 94 of thickness 95 passes radially through cylindrical wall 93. The ablating surface 61 is displaced radially from the center of lumen 101 at distance 96. The width of rectangular region 105 is not constant, but increases to width 107 a distance 108 below the ablating surface 61. The electrode 85 may be fabricated from stainless steel or other suitable material such as titanium.

Figure 31:
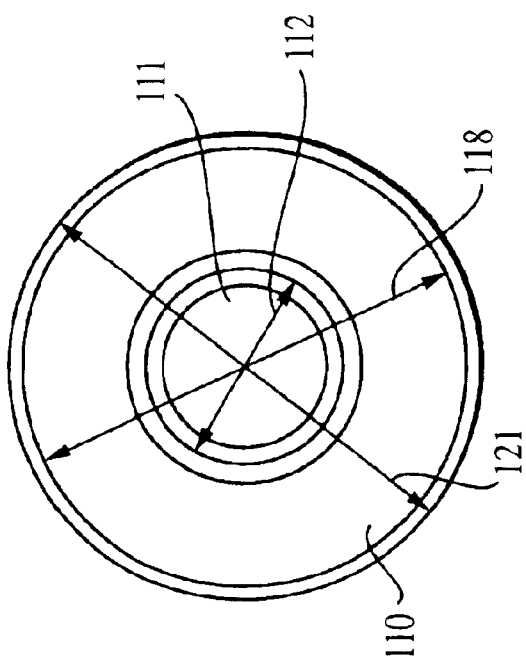
FIG. 31 is an axial view of the tip cap.
Figure 32:
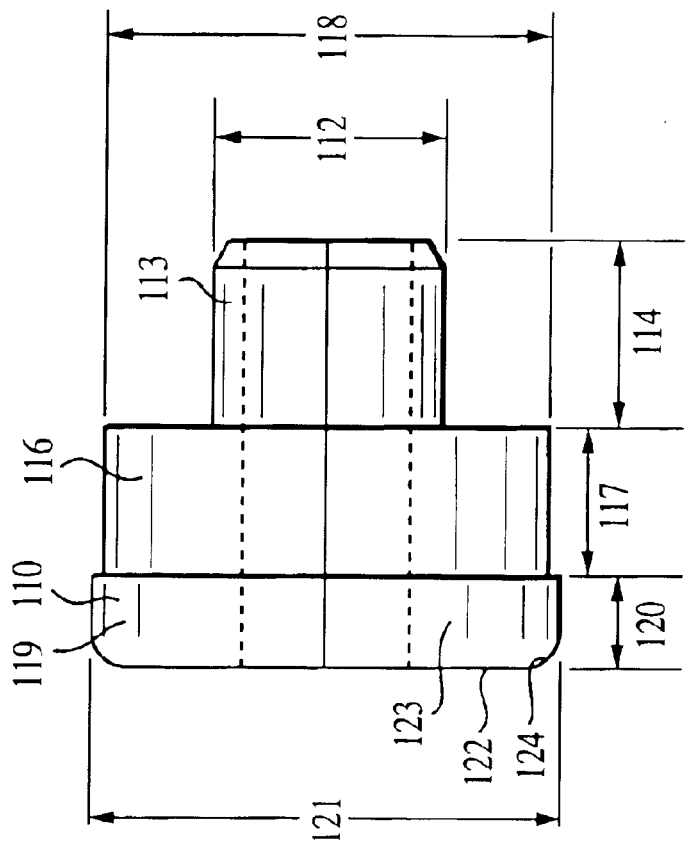
FIG. 32 is a side view of the structure of FIG. 31.

Referring to FIGS. 31 and 32, end cap 110 comprises three coaxial tubular segments, each having an inner lumen 111 of diameter 112. Proximal-most segment 113 of length 114 has a diameter 115 which is slightly greater than diameter 103 of the distal-most segment 102 of inner lumen 76 of mandrel 64. Middle segment 116 of length 117 has a diameter 118 equal to the sum of the diameter 70 of the distal-most portion 68 of the mandrel 64 (FIG. 22) plus twice wall thickness 92 of the electrode 85 (FIG. 29). Distal portion 119 of length 120 has a diameter 121 equal to the diameter 82 of the portion 80 of the mandrel 64. The intersection between distal surface 122 and circumferential surface 123 is formed to a radius 124. The end cap 110 may be formed of a ceramic material such as partially stabilized zirconia, although alumina or another suitable ceramic may be employed also, as desired. The end cap 110 may be also formed of a suitable high-temperature polymeric material, such as PEEK (polyetheretherketone), for example, or other suitable material, as desired.

Referring to FIGS. 33–37, the insulator 62 of length 130 and width 131 has a lower surface 132 formed to a cylindrical radius 133 and a planar upper surface 134 displaced a distance 135 from the axis of cylindrical radius 133. The cylindrical radius 133 is equal to half of diameter 118 of the end cap 110 (FIGS. 31 and 32) and also equal to the sum of half of diameter 70 of the distal-most portion 68 of the mandrel 64 (FIG. 22) plus wall thickness 92 of the electrode 85 (FIG. 29). A rectangular opening 137 extends from the upper surface 134 to the lower surface 132. The rectangular opening 137 has a width 135, which is slightly greater than the width 107 of the electrode 85 (FIG. 30), and a length 136, which is slightly greater than the length 88 of the ablation surface 61 of the electrode 85 (FIGS. 27 and 28). Distal surface 138 of the rectangular opening 137 is displaced a distance 139 from the distal surface 140 of the insulator 62. The distance 139 is slightly smaller than the length 117 of segment 116 of end cap 63 (FIG. 32). Proximal surface 150 of the rectangular opening 137 is displaced a distance 141 from the proximal surface 142 of the insulator 62, the distance 141 being slightly smaller than length 72 of segment 71 of the mandrel 64.

Figure 38:
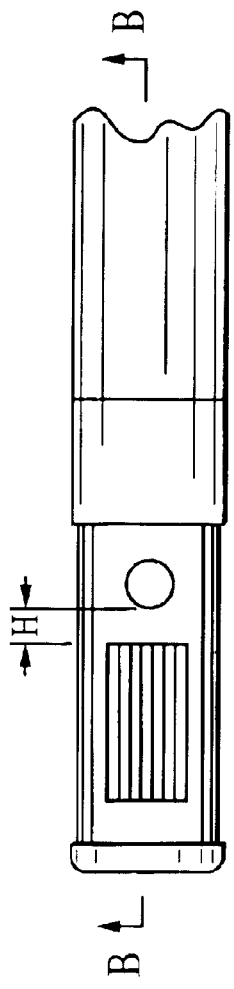
FIG. 38 is a plan view of the ablator tip assembly.
Figure 39:
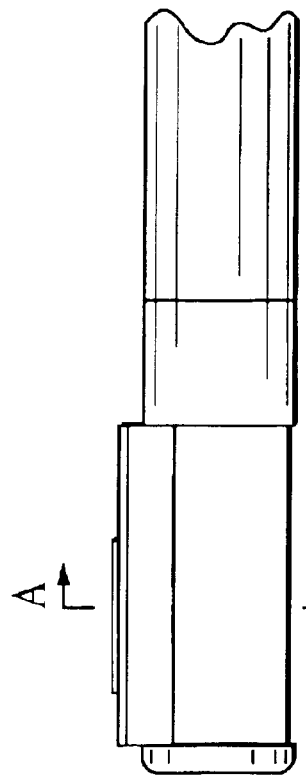
FIG. 39 is a side view of the structure of FIG. 38.
Figure 40:
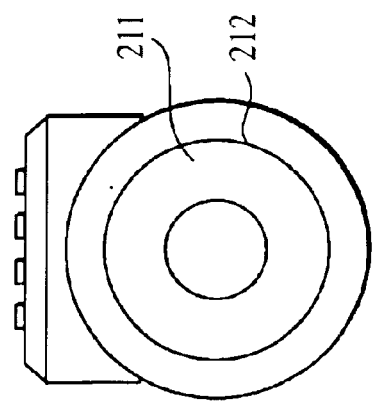
FIG. 40 is an axial view of the structure of FIG. 38.
Figure 46:
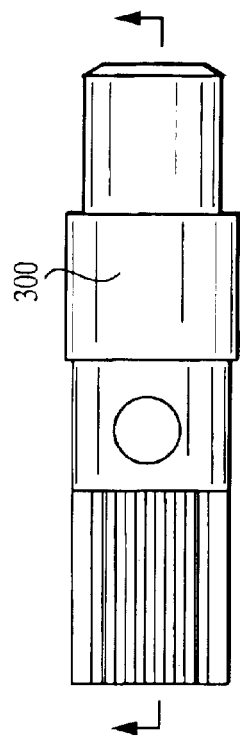
FIG. 46 is a plan view of an alternate embodiment mandrel with integral electrode.
Figure 47:
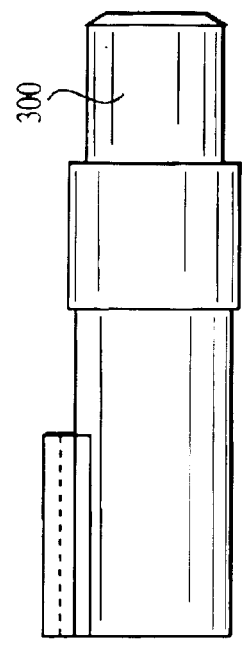
FIG. 47 is a side view of the structure of FIG. 46.
Figure 49:
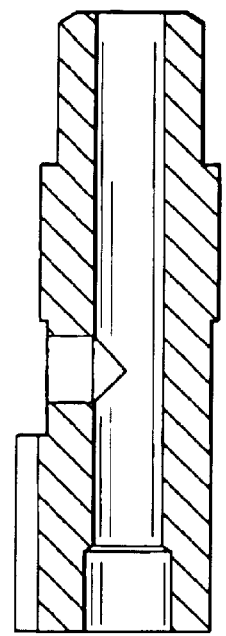
FIG. 49 is a side sectional view along the centerline of the structure of FIG. 46.
Figure 48:
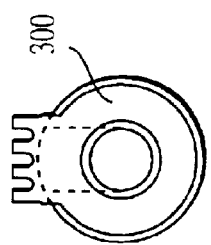
FIG. 48 is a distal end view of the structure of FIG. 46.
Figure 54:
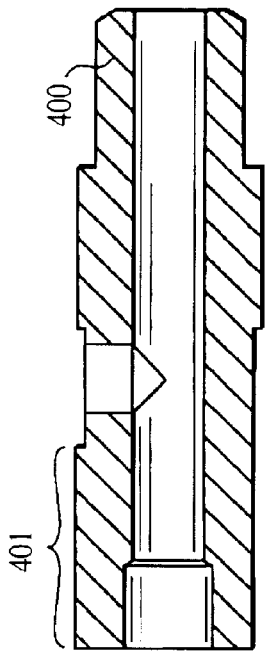
FIG. 54 is a side sectional view along the center of the structure of FIG. 50.
Figure 50:
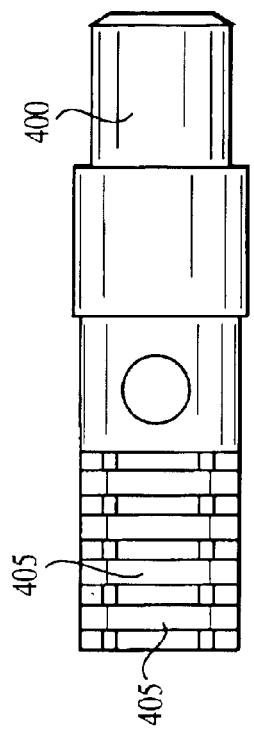
FIG. 50 is a plan view of an alternate embodiment mandrel with integral electrode designed for manufacture on a Swiss-style screw machine.
Figure 51:
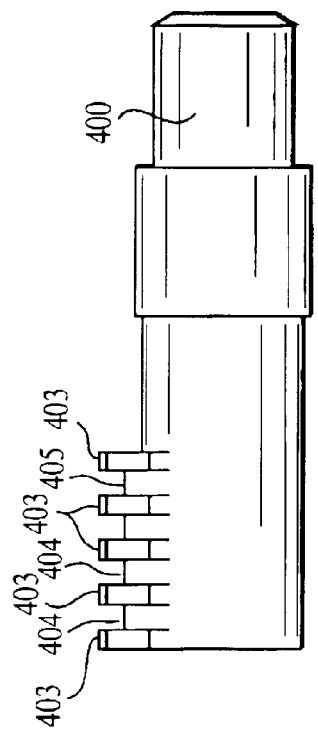
FIG. 51 is a side view of the structure of FIG. 50.
Figure 53:
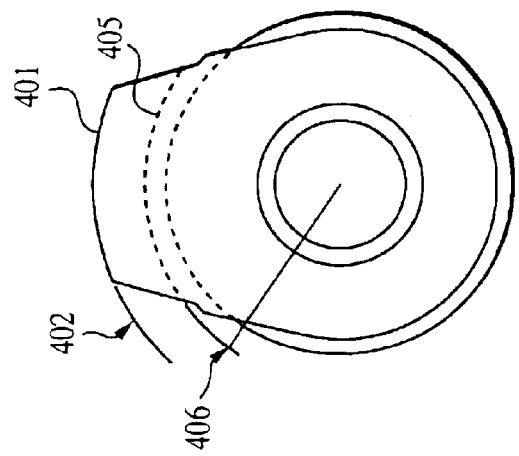
FIG. 53 is an expanded view of the structure of FIG. 50.
Figure 52:
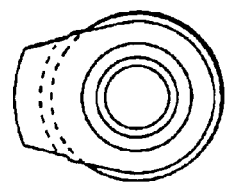
FIG. 52 is a distal end view of the structure of FIG. 50.

A cylindrical passage 144 of diameter 143 extends from the upper surface 134 to the lower surface 132. Diameter 143 is slightly smaller than the diameter 74 of the cylindrical passage 75 of the mandrel 64 (FIG. 22). Cylindrical passage 144 is centered a distance 145 from the proximal surface 142 of the insulator 62, distance 145 being slightly smaller than distance 99 of the mandrel 64 (FIG. 26). The intersection between lateral surfaces 146 and upper surface 134 of the insulator 62 is chamfered a distance 147, although a radius may be substituted. The cylindrical passage 144 is located at a distance "H" (FIGS. 38, 41) from the ablating surface 61. The distance H is preferably less than about 1 cm, more preferably less than about 0.5 cm.

Figure 25:
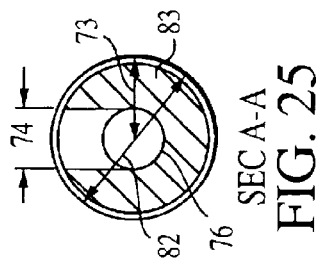
FIG. 25 is an axial sectional view of the structure of FIG. 22 showing the radial aspiration passage.

FIGS. 38–45 illustrate the assembled components of an ablator formed in accordance with the principles of this invention. The mandrel 64 is assembled into the inner lumen 17 of the tube 18, the electrode 85 is assembled onto the mandrel 64, and the tip cap 110 is assembled to the mandrel 64 to form an assembly 200, as shown in FIG. 41. The assembly 200 has a length 205 of constant radius 201, which is equal to the radius 133 of the insulator 62 (FIG. 35) but less than half of diameter 121 of the end cap 110 and less than half of the diameter 82 of the mandrel 64 (FIGS. 23 and 25). The length 205 is greater than the length 130 of the insulator 62 allowing the insulator 62, to be assembled to the assembly of mandrel 64, electrode 85, and end cap 110, as shown in FIGS. 41–45. The insulator 62 is held in place by an epoxy or other suitable adhesive. The difference between length 205 and length 130 of insulator 62 is less than the difference between the length 136 of the rectangular opening 137 in the insulator 62 and the length 88 of the electrode 85 thereby ensuring that, when insulator 62 is positioned as shown in FIG. 41, there will be no contact between distal surface 138 and proximal surface 150 of rectangular opening 137 and electrode 85.

As shown in FIGS. 43 and 44, stepped lateral faces 202 of the electrode 85 prevent contact between the active area of electrode 85 and lateral facing walls 203 of the rectangular opening 137 of the insulator 62. As also shown in FIGS. 41 and 45, the protuberances or ribs 86 protrude above the upper surface 134 of the insulator 62 by a distance "D" of about 0.1 to about 5 millimeters, more preferably of about 0.1 to about 1 millimeters.

Polymeric coating 210 covers exterior surfaces of the assembly 200 consisting of tube 18, mandrel 64, electrode 85, insulator 62 and tip cap 110, except for region 211 (FIG. 40) having a diameter 212 less than diameter 121 (FIG. 32) of tip cap 110 and region 212 (FIGS. 41 and 45) consisting of the ablating surface 61, the top surface 134 of the insulator 62 and a portion of lateral facing and axial facing exterior surfaces of the insulator 62. In this manner, all metallic surfaces are insulated except for the portion of the electrode protruding through the insulator 62. The coating serves two purposes: (i) insulating the assembly from the conductive fluid with which it is surrounded during use; and (ii) securing the insulator 62 and end cap 110 to the mandrel 64. Similarly, dielectric coating 212 covers interior surfaces of metallic components of assembly 200 so as to insulate the assembly from conductive fluids within the inner lumens and connecting passages. As best seen in FIG. 6, coating 212 also covers distal-most surface 213 of alignment connector 40.

In an alternate embodiment (FIGS. 46–49), the mandrel 64 and the electrode 85 are combined in a single component 300 fabricated by metal injection molding.

In another embodiment (FIGS. 50–54), the mandrel 64 and the electrode 85 are combined in a single component 400, which differs from the single component 300 in that the shape of the electrode portion of component 300 is modified so that component 400 can be produced completely in a multi-axis Computer Numerical Control (CNC) Swiss-style screw machine. Electrode surface 401 is cylindrical having a radius 402 and comprises ribs or protuberances 403, which are circumferential and separated by grooves 404, having lower surfaces 405, which are cylindrical and of radius 406. The cylindrical surface 401 can be produced by turning in the screw machine, and the grooves 404 can be produced by a grooving tool in the screw machine so that component 400 may be produced in its entirety in an automatic untended operation. Alternatively, for high production, component 400 may be made by metal injection molding to reduce component costs. The ceramic insert is modified to conform to the contours of component 400.

During use, depressing the "COAG" button on the handle 6 supplies RF energy from the electrosurgical generator via the tubular section to the electrode, the RF energy having a power level appropriate for the removal of fluid from the tissue, causing the tissue to contract and stop bleeding.

Depressing the "ABLATE" button on the handle 6 supplies RF energy of an appropriate waveform and power level for ablation of tissue from the electrosurgical generator via the tubular section to the electrode 85. Because the electrode 85 is insulated except for the ablating surface 61 which protrudes distance D (FIGS. 41 and 45) above the insulator 62, current density at the ablating surface 61 is extremely high and concentrated primarily at the edges of the ribs 86 forming the surface. As with other ablators, the conductive fluid in which the ablator is submerged begins to boil at the ablating surface 61 and, when the bubbles reach a critical size, arcing occurs within the bubbles. When brought into close proximity to tissue, arcs travel from the electrode, through the bubbles to the tissue and tissue contacted by the arcs will be vaporized. Bubbles formed by boiling of the fluid and vaporization of tissue are aspirated from the joint space by flow through the lumen 111 of the end cap 110 and by flow through the passage formed by the cylindrical passage 144 in the ceramic insulator 62 and radial passage 75 of the mandrel 64 which connect to the center lumen 17 of the tubular section 18. Because flow is from the region of ablation but not directly through the active electrode, waste heat rather than process heat is removed and the power level required for effective ablation is not increased by the aspiration. The aspirating flow of water and fluid through the mandrel 64 cools the mandrel 64, and the large mating surface between the active electrode and mandrel cools the electrode, thereby preventing melting of the polymeric insulating material.

The cost of manufacture for the device is low due to its unique construction, that is, by construction from simple, easily and inexpensively machinable components. The tube, mandrel, and alignment/connector are easily produced using a Swiss-style screw machine. The ceramic components are readily produced by ceramic injection molding and the electrode has a simple, two-dimensional shape that is efficiently cut from sheet material by wire EDM. All of the components are maintained in position and alignment by interference between their mating diameters thereby eliminating the need for laser welding or other bonding process.

Although the present invention has been described above with reference to an aspirating ablator electrode having a rectangular ablating region and surface, such as the region 105 and ablating surface 61 of FIG. 29, it must be understood that the present invention is not limited to this embodiment. Accordingly, the present invention also contemplates an aspirating ablator electrode comprising an ablating surface of other geometrical configurations, such as square, triangular, or polygonal, among many others. Of course, the corresponding opening of the surrounding insulator material (such as the rectangular opening 137 of the insulator 62) will have a geometry and shape similar to that of the corresponding ablating surface.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed as new and desired to be protected by Letters Patent of the United States is:

1. A monopolar electrosurgical probe comprising:
   a handle having a proximal end and a distal end;
   a tubular member located at said distal end of said handle and provided with a suction assembly for supplying suction from an external source;
   a mandrel connected to said tubular member and provided with a cylindrical passage;
   a single active electrode mounted on said mandrel, said single active electrode comprising an ablating surface parallel to a longitudinal axis of said mandrel, said ablating surface of said single active electrode comprising a plurality of protuberances; and an insulator in contact with said mandrel and surrounding said ablating surface so that said plurality of protuberances of said ablating surface protrude above a distal longitudinal surface of said insulator.

2. The electrosurgical probe of claim 1, wherein said insulator is provided with at least one opening in communication with said cylindrical passage of said mandrel.

3. The electrosurgical probe of claim 2, wherein said opening of said insulator is located at a distance of less than about 1 cm from said ablating surface.

4. The electrosurgical probe of claim 3, wherein said opening of said insulator is located at a distance of less than about 0.5 cm from said ablating surface.

5. The electrosurgical probe of claim 1, wherein said suction assembly further comprises a control slide mechanism for opening or closing a central lumen of said tubular member.

6. The electrosurgical probe of claim 1, wherein said active electrode further comprises an electrode tubular portion and an active portion in contact with said tubular portion, said active portion being provided with said ablating surface.

7. The electrosurgical probe of claim 6, wherein said active portion has a rectangular configuration.

8. The electrosurgical probe of claim 1, further comprising an insulator cap located at the distal end of said tubular member.

9. The electrosurgical probe of claim 1, wherein said active electrode is integral with said mandrel.

10. The electrosurgical probe of claim 1, wherein said protuberances are oriented in an axial direction relative to said longitudinal axis of said mandrel.

11. The electrosurgical probe of claim 1, wherein said protuberances are oriented in a radial direction relative to said longitudinal axis of said mandrel.

12. The electrosurgical probe of claim 1, wherein said plurality of protuberances protrude for about 0.1 to about 5 millimeters.

13. The electrosurgical probe of claim 1, wherein said protuberances are spaced from each other by a predetermined distance.

14. The electrosurgical probe of claim 13, wherein said predetermined distance is of about 0.1 to about 2 millimeters.

15. The electrosurgical probe of claim 14, wherein said predetermined distance is of about 0.2 to about 0.4 millimeters.

16. The electrosurgical probe of claim 1, wherein said protuberances have a cross-sectional shape selected from the group consisting of rectangular, square, trapezoidal, triangular and hexagonal shape.

17. A monopolar electrosurgical system for the electrosurgical treatment of tissue immersed in a conductive fluid comprising:
 a power supply source; and
 means for applying high frequency voltage to an electrosurgical probe, said electrosurgical probe comprising:
 a tubular member provided with a suction assembly for supplying suction from an external source;
 a mandrel connected to said tubular member and provided with a cylindrical passage;
 a single active electrode mounted on said mandrel and comprising at least one ablating surface parallel to a longitudinal axis of said mandrel, said at least one ablating surface of said single active electrode comprising a plurality of protuberances;
 a dielectric material in contact with said mandrel and surrounding said ablating surface so that said plurality of protuberances of said ablating surface protrude above a distal longitudinal surface of said dielectric material;
 an aspiration port connected to said suction assembly and disposed on said mandrel at a different location than said single active electrode.

18. The electrosurgical system of claim 17, wherein said dielectric material is provided with at least one opening in communication with said cylindrical passage of said mandrel.

19. The electrosurgical system of claim 18, wherein said opening is located at a distance of less than about 1 cm from said ablating surface.

20. The electrosurgical system of claim 17, wherein said suction assembly further comprises a control slide mechanism for opening or closing a central lumen of said tubular member.

21. The electrosurgical system of claim 17, wherein said active electrode further comprises an electrode tubular portion and an active portion in contact with said tubular portion, said active portion being provided with said ablating surface.

22. The electrosurgical system of claim 17 further comprising an insulator tip located at the distal end of said tubular member.

23. The electrosurgical system of claim 17, wherein said active electrode is integral with said mandrel.

24. The electrosurgical system of claim 17, wherein said protuberances are oriented in an axial direction relative to said longitudinal axis of said mandrel.

25. The electrosurgical system of claim 17, wherein said protuberances are oriented in a radial direction relative to said longitudinal axis of said mandrel.

26. The electrosurgical system of claim 17, wherein said plurality of protuberances protrude for about 0.1 to about 5 millimeters.

27. A method of conducting an electrosurgical procedure comprising the steps of:
 providing an active electrode of an electrosurgical probe, said active electrode comprising a body region surrounded by a dielectric material and an ablating surface adjacent said body region, said ablating surface being parallel to a longitudinal axis of a suction assembly provided within a mandrel, said ablating surface being located at less than about 1 cm from an opening of said dielectric material, said opening being in communication with said suction assembly;
 positioning said active electrode in the proximity of a tissue to be treated in the presence of an electrically conductive fluid;
 applying a high frequency voltage to said active electrode to generate an electric field adjacent said ablating surface;
 activating said suction assembly for supplying suction from an external source; and
 effecting ablation of at least a portion of said tissue to be treated.

28. The method of claim 27, wherein said step of activating said suction assembly further comprises controlling the opening or closing of at least one passage of said suction assembly, said passage allowing flow of debris from said tissue to be removed.

29. The method of claim 27, wherein said ablating surface is provided with a plurality of protuberances that protrude above said dielectric material by about 0.1 to about 5 millimeters.

* * * * *